United States Patent
Galizia

(10) Patent No.: US 10,317,352 B2
(45) Date of Patent: Jun. 11, 2019

(54) MACHINE FOR TESTING THERMAL RESISTANCE OF PLASTIC MATERIALS, IN PARTICULAR THERMOPLASTIC POLYMERS

(71) Applicant: ILLINOIS TOOL WORKS INC., Glenview, IL (US)

(72) Inventor: Giuseppe Galizia, Turin (IT)

(73) Assignee: Illinois Tool Works Inc., Glenview, IL (US)

( * ) Notice: Subject to any disclaimer, the term of this patent is extended or adjusted under 35 U.S.C. 154(b) by 108 days.

(21) Appl. No.: 15/478,603

(22) Filed: Apr. 4, 2017

(65) Prior Publication Data

US 2017/0284950 A1 Oct. 5, 2017

(30) Foreign Application Priority Data

Apr. 5, 2016 (IT) .................. 102016000034798

(51) Int. Cl.
| | | |
|---|---|---|
| *G06F 11/30* | (2006.01) | |
| *G01N 25/18* | (2006.01) | |
| *G01N 33/28* | (2006.01) | |
| *G01N 3/42* | (2006.01) | |
| G01N 25/04 | (2006.01) | |
| G01N 33/44 | (2006.01) | |

(52) U.S. Cl.
CPC ............ *G01N 25/18* (2013.01); *G01N 3/42* (2013.01); *G01N 33/2805* (2013.01); G01N 25/04 (2013.01); G01N 33/442 (2013.01); G01N 2203/02 (2013.01); G01N 2203/0202 (2013.01); G01N 2203/0226 (2013.01)

(58) Field of Classification Search
CPC ..................................................... G01N 25/18
See application file for complete search history.

(56) References Cited

FOREIGN PATENT DOCUMENTS

DE 10026223 * 1/2001

OTHER PUBLICATIONS

Anonymous: "Ceast Hot Vicat Series 3 and 6 Stations Testers", Jan. 1, 2012 (Jan. 1, 2012), XP 055325318, Retrieved from the Internet: URL: http//www.instron.us/>>/media/lieterature-library/products/2012/06/pod-ceast-hdt-vicat-series-3-and-6-stations-testers.pdf? la=en [retrieved on Dec. 1, 2016] (submitted by Applic.*

(Continued)

*Primary Examiner* — Phuong Huynh
(74) *Attorney, Agent, or Firm* — Lando & Anastasi, LLP

(57) ABSTRACT

Machine for testing thermal resistance of plastic materials, comprising a tank configured, in use, to be filled for example with a heat-transfer fluid; a heating coil for heating the heat-transfer fluid; a temperature sensor generating a temperature signal of the heat-transfer fluid; and a control unit calculating a degradation index of the heat-transfer fluid on the basis of the temperature signal. In particular, the degradation index is calculated by determining the temperature range associated with the temperature signal, updating the corresponding partial heating time, and calculating the weighted sum of the partial heating times previously saved in memory and pertaining to different temperature ranges. Upon reaching one or more thresholds, signals are generated which indicate the need to replace the heat-transfer fluid.

13 Claims, 3 Drawing Sheets

(56) References Cited

OTHER PUBLICATIONS

Anonymous: "Ceast Hot Vicat Series 3 and 6 Stations Testers", Jan. 1, 2012 (Jan. 1, 2012 ), XP055325318, Retrieved from the Internet: URL:http://www.instron.us/>>/media/literature-library/products/2012/06/pod-ceast-hdt-vicat-series-3-and-6-stations-testers.pdf?la=en [retrieved on Dec. 1, 2016].
Italian Search Report and Written Opinion from corresponding Italain Application No. ITUA20162307 dated Dec. 8, 2016.

\* cited by examiner

| Table 1 | | | |
|---|---|---|---|
| Temperature range (°C) | Range No. | Limit value [h] | Counter |
| 0 - 40 | I1 | No limit | No counting |
| 40 - 199 | I2 | $N_1 = 19000$ | $n_1$ |
| 199 - 230 | I3 | $N_2 = 14200$ | $n_2$ |
| 230 - 259 | I4 | $N_3 = 9600$ | $n_3$ |
| 259 - 300 | I5 | $N_4 = 5000$ | $n_4$ |

MACHINE FOR TESTING THERMAL RESISTANCE OF PLASTIC MATERIALS, IN PARTICULAR THERMOPLASTIC POLYMERS

PRIORITY CLAIM

This application claims priority from Italian Patent Application No. 102016000034798 filed on Apr. 5, 2016, the disclosure of which is incorporated by reference.

TECHNICAL FIELD

The present invention concerns a machine for testing the thermal resistance of plastic materials, especially thermoplastic polymers.

BACKGROUND OF THE INVENTION

As is known, for such applications, for example in the automotive industry, it is required that the plastic materials to be sold be accompanied by a declaration certifying their characteristics, in particular, their temperature resistance under load, by providing their values of flexure and deformation under predetermined test conditions. In particular, numerous international standards exist which regulate these test conditions, such as the standards ISO 75 (part 1 and 2), ISO 306, ASTM D648 and ASTM D1525 respectively for the HDT tests (Heat Deflection Temperature) and the Vicat tests.

Specifically, in the HDT test, one measures the stress induced in a specimen subjected to a flexural load at 3 points. To this end, the specimen is subjected to a load of predetermined value, for example by way of a bar-shaped head; it is then heated gradually and in controlled manner (2° C. per minute) until reaching a predetermined deflection (0.25 mm for the ASTM test or a value between 0.32 and 0.36 mm for the ISO test). The temperature value at which this deflection is reached represents the HDT value.

In the Vicat test, or softening test, one measures the temperature at which a circular indenter with a cross section of 1 $mm^2$, subjected to a predetermined load, penetrates by 1 mm into the specimen.

For the performance of such tests, as set forth by the standard, the specimen is first secured to a support and immersed in a liquid able to transfer heat under the indicated controlled conditions.

Hence, for some time, test machines have been available on the market having a tank filled with a heat-transfer fluid, typically silicone oil, which is heated and cooled by means of coils and fans so as to provide the required heating ramps of the test. In such machines, a specimen secured to a support is immersed in the tank of oil and subjected to the action of the load (in the HDT test) or the indenter (in the Vicat test). The deformation of the specimen is measured as a movement of a rod secured to the load or carrying the indenter; as soon as the rod moves by the value specified in the standard, the current temperature value of the heat transfer oil is acquired, representing the HDT value or the softening value, depending on the type of test. At the end of the test, the oil is cooled down so that another test can be performed on a different specimen.

In the testing machines of the type under consideration, therefore, the heat transfer oil undergoes many cycles of heating (up to 290° C.) and cooling which, over time, degrade its characteristics, especially its viscosity. Thus, after a certain time, the heat transfer oil deteriorates and needs to be replaced, in order to assure the proper heating of the specimen and therefore proper performance of the tests.

With the current testing machines, however, the determination of the time at which the heat transfer oil deteriorates is not possible with precision. In fact, tables provide the deterioration times of the heat transfer oil as a function of certain temperature values. But these do not take into account the variability of the temperature during the tests and do not provide degradation values at different temperatures. Consequently, such tables are not directly useful with the testing machines under consideration, given the above-described cycles of heating and cooling.

SUMMARY OF THE INVENTION

The aim of the present invention therefore consists in overcoming the drawbacks of the prior art machines.

According to the present invention, a testing machine and method for testing the thermal resistance of plastic materials are provided, as defined in the accompanying claims.

BRIEF DESCRIPTION OF THE DRAWINGS

For a better understanding of the present invention, preferred embodiments shall now be described, merely as a non-limiting example, with reference to the accompanying drawings, in which.

DETAILED DESCRIPTION OF THE INVENTION

Figure 1:
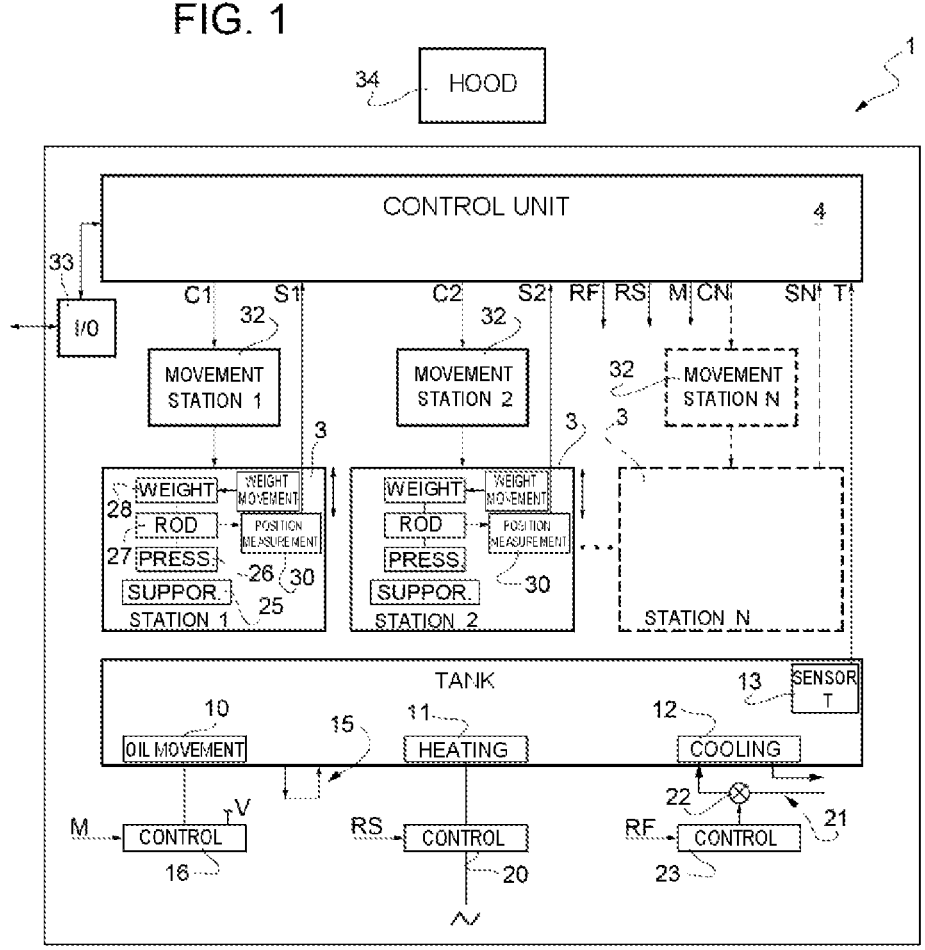
FIG. 1 is a block diagram of a testing machine for plastic material according to an embodiment of the invention.

FIG. 1 shows in general the structure of a testing machine 1 designed to carry out HDT tests and Vicat tests for plastic materials.

The testing machine 1 comprises a tank 2, a plurality N of stations 3, and a control unit 4.

The tank 2, when in use, is filled with a heat-transfer fluid, typically oil, such as silicone oil.

Inside the tank 2 there are provided an oil movement system 10; an oil heating system 11; an oil cooling system 12 and a temperature sensor 13.

The oil movement system 10 has the purpose of ensuring an approximately uniform temperature at all points of the tank, at least at the level of the specimen supports (see below). In general, it is also possible to have a temperature variation which is not entirely uniform, for example, one with a triangular shape for the various stations 3; in this case, any offset can be compensated by an algorithm, if necessary.

The oil movement system 10 is typically formed by a motor (not shown) which operates a plurality of vanes or blades (not shown) arranged at the bottom of the tank 2 and which, when in use, draw in and push the heat transfer oil toward a recirculating system, shown only schematically and indicated as 15. The oil movement system 10 is operated by a movement driving device 16, controlled by the control unit 4 via an oil control signal M.

The oil heating system 11 comprises, for example, resistive coil elements (not shown), connected to a heating driving device 20 controlled by the control unit 4 by a heating control signal R.

The oil cooling system 12 comprises for example a coiled conduit (not shown) arranged on the walls of the tank and connected to a cooling circuit 21, shown only schematically. The cooling circuit 21 has cooling water flowing through it, for example, and is opened or closed by an electric valve 22 controlled by a cooling driving device 23, controlled by the control unit 4 by a cooling control signal RF.

The temperature sensor 13 is comprised, for example, of an armored thermistor and it provides a temperature signal T to the control unit 4.

Each station 3 comprises a support 25 designed to hold a respective specimen; a pressing element 26; a rod 27 secured to the pressing element 26; a weight 28 applied to the rod 27; and a weight movement assembly 29. In detail, the pressing element 26 is typically an indenter, or a circular indenter, when the specific station 3 is designed to perform a Vicat test, or a bar of definite shape, when the specific station 3 is designed to perform a HTD test, such as per se known. Prior to the test, the weight 28 is applied to the rod 27 by the weight movement assembly 29 which picks up the weight and possibly other additional masses from a plate (not shown). The weight movement assembly 29 can be a simple leverage, manually controlled for each station 3, as shown. Alternatively, the weight movement assembly 29 can be controlled by a single motor for all the stations 3, under the control of the control unit 4.

Each station 2 furthermore comprises an own position detection device 30, associated with the respective rod 27 and designed to measure its displacement. The position detection device 30 may work by any suitable physical principle; for example, it may be an inductive position transducer, in particular a variable linear differential transformer, having a core integrated with the rod 27, in order to generate a position signal S1, S2, . . . , SN provided to the control unit 4.

In use, the stations 2 are movable from a raised position, in which the respective supports 10 are outside the tank 3 and it is possible to secure the specimens, and a lowered position, in which these supports 10 (and the respective specimens) are completely immersed in the heat transfer oil which in the tank 3.

In the shown sample embodiment, N station movement assemblies 32 are provided for the movement of the stations 3, one for each station 3. In this case, each station movement assembly 32 comprises a raising and lowering mechanism, controlled manually or, via N motors, by the control unit 4, as shown in FIG. 1, via a station movement signal C1, C2, . . . , CN. With this solution, the raising or lowering of each station 3 can be controlled individually and at different times, if so desired and provided for. Alternatively, there can be a single motor controlled by the control unit 4, which brings about the raising or lowering of all the stations 3 at the same time.

Input/output I/O units 33 are connected to the control unit 4, for interaction with a technician, in particular for the acquisition of control signals, the display of information, such as the test status, and the generation of alarm signals, as described below in further detail, as far as relevant to the present description. The input/output units 33 may comprise a screen, a keypad, a printer, a panel having display areas and pushbuttons, an audible warning, a data exchange line, etc.

A hood 34 is usually arranged above the test machine 1 for sucking noxious fumes.

Figure 2:
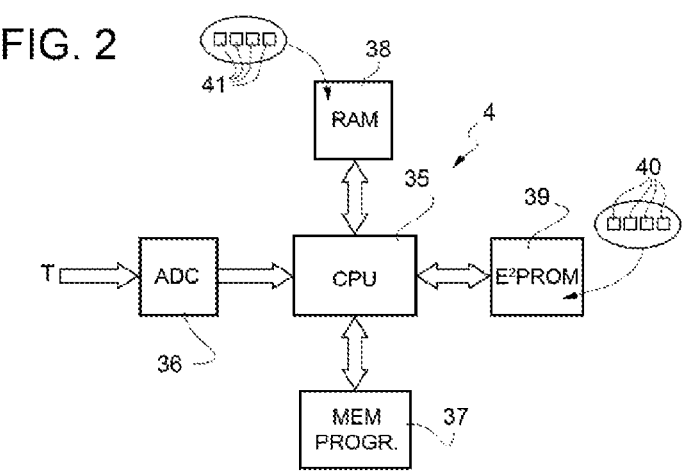
FIG. 2 is a block diagram of part of the testing machine of FIG. 1.

The control unit 4 commands and controls all the automatic operations performed by the test machine 1 on the basis of the settings and the commands provided by the user and comprises substantially a microcontroller of commercial type having, as far as relevant to the present description, the block structure shown in FIG. 2.

In detail, the control unit 4 comprises a processor 35 connected to an analog/digital converter 36 receiving the temperature signal T, a program memory 37, such as of flash type, a working memory 38, such as a RAM, and a non-volatile memory 39, such as an EEPROM.

In particular, the control unit 4 periodically verifies the degradation state of the heat transfer oil in the tank 2 by estimating it on the basis of the previous heating times and the current temperature, using an algorithm described below. Based on the estimated values and through the I/O units 33, the control unit 4 generates corresponding signals to the user. In particular, the control unit 4 signals to the user when the degradation situation of the heat transfer oil is elevated, so as to foresee a need to replace it in the near future, and also when the heat transfer oil has degraded to such an extent as to require an immediate replacement (at the end of the test). Obviously, the control unit 4 can display at each instant the estimated degradation condition and generate various signal levels, optionally preventing the performance of further tests (while allowing the present test to be completed) in case of exceeding a predetermined level and/or generate acoustic type alarms.

To this end, the control unit 4 operates according to a degradation verification method which counts the time spent by the heat transfer oil in various temperature zones, stores these times, and calculate the degradation degree as the normalized sum of the various counts, taking into account the characteristics of the heat transfer oil as provided by experimental data from the manufacturer.

In particular, for the silicone oils usable in a testing system for plastic materials of the type considered, two experimental values are defined (hereinafter designated as $t_1$ and $t_2$), known as the "gel time", representing the time needed to reach a state transition due to the complete oxidation of the silicone oil while working at two predetermined temperatures. For example, for the silicone oil Xiameter PMX-0210 produced by the Dow Corning Corporation, the two experimental values of the gel time are the following: $t_1$=19,000 hours for an operating temperature of the silicone oil of 199° C., and $t_2$=5000 hours for an operating temperature of the silicone oil of around 288° C.

However, these two experimental values do not describe the degradation state of the heat transfer oil in the entire range of operating temperatures used in the testing machine 1, which can vary between ambient temperature and 300° C.

In order to have a more correct evaluation of the degradation, the present method supposes that the degradation behavior (time) of the heat transfer oil has a linear variation between the two experimental values $t_1$, $t_2$ indicated by the manufacturer (hereinafter also indicated as the experimental limit times) and it divides the temperature interval between these experimental values into several intervals. For example, according to an embodiment of the present method, as shown in the chart of FIG. 3, the interval defined by the above-indicated gel times is divided into three parts and the intermediate values of the gel time (also indicated as interpolated limit values) corresponding to the limits of the chosen intervals (in the example shown, 259° C. and 230° C.) are interpolated, obtaining the values, respectively, of 9600 h and 14,200 h.

Figures 3, 4:
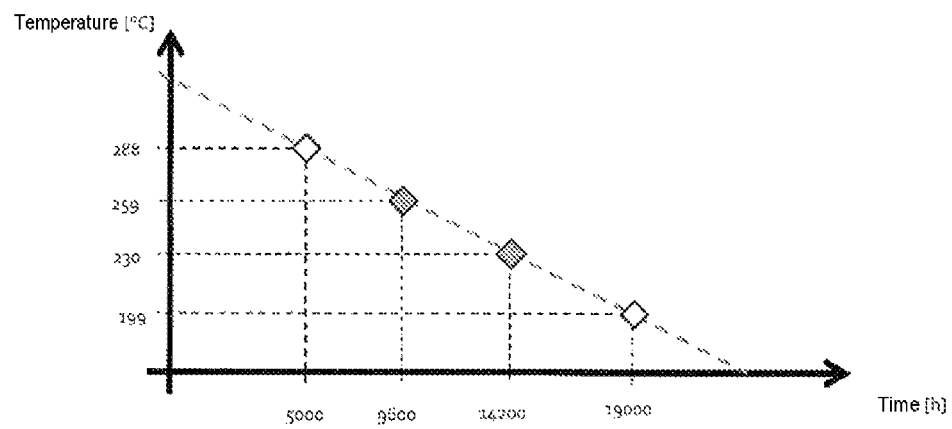
FIG. 3 shows a chart used to determine limit values of a silicone oil as a function of the operating temperature.
FIG. 4 shows a table of limit values associated with various operating temperature ranges.

Thus, starting with the experimental and interpolated gel time values, the present method defines two further temperature ranges (operating temperature less than 40° C., beneath which the degradation is considered to be insignificant, and operating temperature between 40° C. and 199° C.), and associates respective degradation limit values $N_1$, $N_2$, $N_3$, $N_4$ with each range, according to Table 1, shown in FIG. 4. Moreover, the present method associates a counter with each of the ranges characterized by degradation, indicated as I1, I2, I3, I4, and also indicated in Table 1.

In use, the control unit 4 periodically acquires the instantaneous temperature value T, increments the counter of the temperature range including the measured value, and updates an oil degradation index N defined as the sum of the values counted by the counters, each being normalized with respect to its own limit value, according to the equation:

$$N = n_1/N_1 + n_2/N_2 + n_3/N_3 + n_4/N_4 \quad (1).$$

In general, with k temperature ranges, the index of degradation N is given by:

$$N = \sum_{i=1}^{k} \frac{n_i}{N_i}$$

This index is calculated as a percent, since it should always be less than 1. Upon reaching an alert value, such as 80%, a first warning message is generated; upon reaching 100%, a message is generated calling for requesting assistance for replacing the heat transfer oil, which is degraded, or for replacing it.

Figure 5:
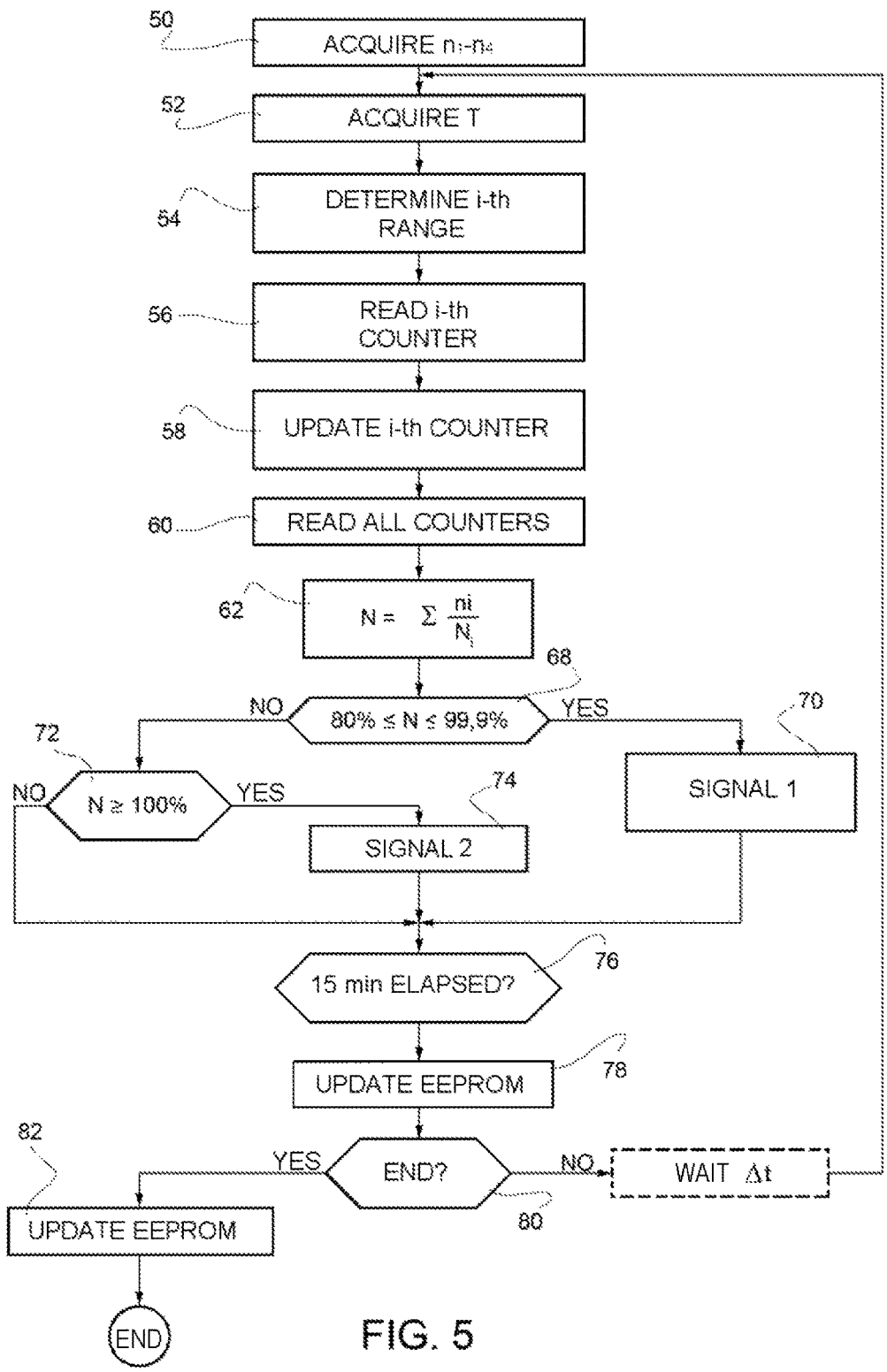
FIG. 5 is a flow chart of the method for monitoring the degradation of the heat-transfer fluid in the machine of FIG. 1.

With specific reference to FIG. 2, the control unit 4 implements the method of determination of the degradation state of the heat transfer oil as shown in the flow chart of FIG. 5.

In detail, upon turning on the testing machine 1, the processor 35 reads the count values $n_1$, $n_2$, $n_3$, $n_4$ regarding previous tests from respective locations 40 of the nonvolatile memory 39 and loads them into as many other locations 41 in the working memory 38, forming dynamic counters, step 50. Then, every minute, the processor 35 acquires the present temperature value T, as digitized in the analog/digital converter 36, step 52; determines the temperature range I1-I5 of the just acquired value, step 54; reads the corresponding degradation value $n_i$ stored by the respective i-th counter 41 in the working memory 38, step 56; updates the degradation value $n_i$, by adding the time $\Delta t$ elapsed since the previous detection (in the present case, 1 minute) to the value read by the counter 41 and writing the result of the sum into the same counter 41, step 58; reads all the degradation values $n_1$-$n_4$, step 60, and calculates the oil degradation index N according to eq. (1), given above, step 62.

The processor 35 then verifies whether the index N just calculated is within 80% and 99.9%, step 68. In this case (output YES of step 68), the processor 35 controls sending of a notice, such as the displaying of the message "Oil approaching its expiration date", step 70. If not (output NO of step 68), the processor 35 verifies whether the just calculated index N is greater than 99.9%, step 72. In this case (output YES of step 72), the processor 35 controls sending of a second notice, such as displaying of the message: "Oil lifetime expired", step 74. If not (output NO of step 72), and in any case after steps 70 and 74, the processor 35 verifies whether a particular time has passed (such as 15 min) from the last saving of the oil degradation index N in the nonvolatile memory 39, step 76, and if so (output YES of step 76) it updates it, step 78.

The processor 35 then verifies whether the test phase is finished, step 80, and if so (output YES of step 80) it stores the value of all the counters n1, n2, n3, n4 in the nonvolatile memory 39, step 82, and ends the process. If not (output NO of step 80), after a waiting time, the processor 35 returns to step 52 in order to acquire a new instantaneous value T of the temperature from the A/D converter 36.

The machine and the method described here have numerous advantages.

In particular, they allow for a steady monitoring of the degradation state of the heat transfer oil and generation of appropriate messages. In this way, the technician can schedule maintenance and oil replacement actions, enabling a more efficient management of the machine and without risks of operation shutdown. Moreover, it is assured that the performed tests are indeed correct, and not affected by the degradation of the heat-transfer fluid on account of evaluation errors or forgetfulness.

Monitoring is done automatically and in reliable manner, without requiring added costs, and thus without increasing the production and management costs of the test machine.

Finally, it is clear that modifications and variants can be made in the machine and the method described and illustrated here, without thereby departing from the scope of the present invention, as defined in the appended claims. For example, although the preceding description refers to heating by silicone oil, the same solution is applicable to any other fluids suitable for heat transfer.

Moreover, the described algorithm can be modified in various ways, for example by storing the different limit degradation values N1, N2, N3, N4 in an appropriate table saved in the nonvolatile memory 39 for different types of heat-transfer fluid and reading these values on the basis of the settings. Furthermore, additional signal sending thresholds can be provided.

The calculation of the sum of the normalized values of the counting times can be considered to be a particular case of the weighted sum of these values; as an alternative, in particular, each counting time may be multiplied by a corresponding weight, associated with the respective temperature range.

What is claimed is:
1. A machine for testing thermal resistance of plastic materials, comprising:
 a tank (2) configured, in use, to be filled with a heat-transfer fluid,
 means (11) for heating the heat-transfer fluid,
 a temperature sensor (13) configured to generate, in use, a temperature signal (T) of the heat-transfer fluid, having a value, and
 a control unit (4) for monitoring degradation of the heat-transfer fluid over a plurality of temperature ranges, the control unit configured to receive the temperature signal (T), count a plurality of partial heating times, each partial heating time being related to a heating time of the heat-transfer fluid in a respective temperature range of the plurality of temperature ranges, the control unit (4) comprising a plurality of memory elements (41), each memory element being configured to store a respective partial heating time, and the control unit being configured to calculate a degradation index (N) related to the lifetime of the heat-transfer fluid based on a weighted sum of the plurality of partial heating times.

2. The test machine according to claim 1, wherein the control unit (4) is a microcontroller and comprises a processor (35) and a volatile memory unit (38) including the plurality of memory elements (41), the processor (35) being configured to receive (52) the value of the temperature signal (T), read (56) the partial heating time stored in the memory element associated with the temperature range corresponding to the value of the temperature signal, update (58) the stored partial heating time, read (60) the partial heating times of all of the memory elements, and calculate (62) the degradation index by adding the partial heating times.

3. The test machine according to claim 1, wherein the degradation index is calculated according to the equation:

$$N = \sum_{i=1}^{k} \frac{n_i}{N_i}$$

wherein k is the number of temperature ranges, $n_i$ is the corresponding partial heating time and $N_i$ is a maximum degradation value associated with each temperature range.

4. The test machine according to claim 1, wherein the control unit (4) is configured to generate warnings (70; 72) when the degradation index of the heat-transfer fluid reaches preset threshold values.

5. The test machine according to claim 2, wherein the control unit (4) comprises a non-volatile memory (39) configured to periodically store the partial heating times.

6. A method for determining degradation of a heat-transfer fluid over a plurality of temperature ranges in a machine (1) for testing thermal resistance characteristics of plastic materials, the test machine having means for heating the heat-transfer fluid, the method including:
   acquiring (52) a temperature signal (T) of the heat-transfer fluid having a value,
   determining (54) a temperature range associated with the value of the temperature signal (T) from the plurality of temperature ranges,
   updating (58) a partial heating time related to the selected temperature range,
   acquiring (60) partial heating times for each temperature range in the plurality of temperature ranges, and
   calculating (54-62) a degradation index related to the lifetime of the heat-transfer fluid based on a weighted sum of the partial heating times.

7. The method according to claim 6, wherein the calculating the degradation index phase (62) uses equation:

$$N = \sum_{i=1}^{k} \frac{n_i}{N_i}$$

wherein k is the number of temperature ranges, $n_i$ is the partial heating time in each temperature range and $N_i$ is a maximum degradation value associated with each temperature range.

8. The method according to claim 6, including storing (58) the updated partial heating time by volatile memory writing, wherein acquiring (60) partial heating times for each temperature range comprises reading a plurality of cells (41) of a volatile memory (38) each associated with a respective temperature range in the plurality of temperature ranges.

9. The method according to claim 6, also including generating (70, 72) a warning when the degradation index of the heat-transfer fluid reaches preset threshold values.

10. The method according to claim 6, wherein acquiring (52) a temperature signal and calculating (54-62) a degradation index are carried out periodically with a monitoring time interval (Δt) and updating the partial heating time comprises acquiring a previous stored partial heating time and adding the monitoring time interval.

11. The method according to claim 6, further comprising periodically saving (78) the partial heating times in a non-volatile memory (39).

12. The method according to claim 6, further including:
   acquiring experimental gel-time values associated with two experimental heating temperatures of the heat-transfer fluid,
   using the experimental gel-time values as maximum degradation values associated to the respective temperature ranges including both experimental temperatures, and
   calculating further maximum degradation values as linear interpolations of the experimental gel-time values.

13. A program product for a processor configured to implement, when loaded onto processing means, the method according to claim 6.

* * * * *